United States Patent [19]
Hill et al.

[11] Patent Number: 5,972,351
[45] Date of Patent: Oct. 26, 1999

[54] *PLASMODIUM FALCIPARUM* MHC CLASS I-RESTRICTED CTL EPITOPES DERIVED FROM PRE-ERYTHROCYTIC STAGE ANTIGENS

[75] Inventors: Adrian Vivian Sinton Hill; Frances Margaret Gotch; John Elvin, all of Oxford; Andrew James McMichael, Horton-cum-Studley; Hilton Carter Whittle, The Gambia, all of United Kingdom

[73] Assignee: Isis Innovation Limited, Oxford, United Kingdom

[21] Appl. No.: 08/318,856

[22] PCT Filed: Apr. 5, 1992

[86] PCT No.: PCT/GB93/00711

§ 371 Date: Dec. 5, 1994

§ 102(e) Date: Dec. 5, 1994

[87] PCT Pub. No.: WO93/20103

PCT Pub. Date: Oct. 14, 1993

[30] Foreign Application Priority Data

Apr. 3, 1992 [GB] United Kingdom .................. 9208068
Aug. 20, 1992 [GB] United Kingdom .................. 9217704

[51] Int. Cl.[6] ....................... A61K 39/015; A61K 39/00; A61K 38/04
[52] U.S. Cl. ................................... 424/272.1; 424/191.1; 530/328
[58] Field of Search ......................... 435/258.2; 530/320; 424/185.1, 272.1

[56] References Cited

FOREIGN PATENT DOCUMENTS

0398540A1 11/1990 European Pat. Off..
0432965A1 6/1991 European Pat. Off..

OTHER PUBLICATIONS

Zevering et al., Intl. Immunol. 2:945–955, 1990.
Falk et al., Nature 351:290–296, 1991.
Elvin et al., Eur. J. Immunol. 21:2025–2031, 1991.
Jardetzky et al., Nature 353:326–329, 1991.
Shirai et al., J. Immunol. 148:1657–1667, 1992.
Eisenlohr et al., J. Exp. Med. 175:481–487, 1992.
Del Val et al., Cell 66:1145–1153, 1991.
Galinski et al., Parasitol. Today 12:20–29, 1996.
Cox, TIBTECH 9:389–394, 1991.
Lalvani et al., Res. Immunol. 145:461–468, 1994.
Udhayakumar et al., Infect. Immun. 62:1410–1413, 1994.
D.F. Nixon et al., "Cytotoxic T–Cell Recognition of HIV Proteins and Peptides," *Aids 1991*, vol. 5, No. 9, pp. 1049–1059 (Jul. 1991).
B.H. Hahn et al., "Relation of HTLV–4 to Simian and Human Immunodeficiency–Associated Viruses," *Nature*, vol. 300, pp. 184–186 (Nov. 1987).
K. Falk et al., "Allele–Specific Motifs Revealed by Sequencing of Self–Peptides Eluted from MHC Molecules," *Nature*, vol. 351, pp. 290–296 (May 1991).
J. Elvin et al., "A Quantitative Assay of Peptide–Dependent Claim I Assembly," *European Journal of Immunology*, vol. 21, pp. 2025–2031 (1991).
P. Romero et al., "Isolation and Characterization of Protective Cytolytic T Cells in a Rodent Malaria Model System," *Immunology Letters*, vol. 25, pp. 27–32 (1990).

*Primary Examiner*—Laurie Scheiner
*Assistant Examiner*—Jeffrey S. Parkin
*Attorney, Agent, or Firm*—Wenderoth, Lind & Ponack, L.L.P.

[57] ABSTRACT

A method of identifying peptides of an antigen of interest which are capable of recognition by or induction of cytotoxic T lymphocytes, comprises the steps of: ascertaining a "motif" of peptides which bind to a chosen HLA class I allele; providing peptides having this motif which are present in the known sequence of the antigen of interest; screening the peptides using an HLA assembly assay; and screening the resulting peptides for recognition by or induction of cytotoxic T lymphocytes. The above peptides have been identified by this method, and the peptides and vaccines containing them are also claimed.

2 Claims, 4 Drawing Sheets

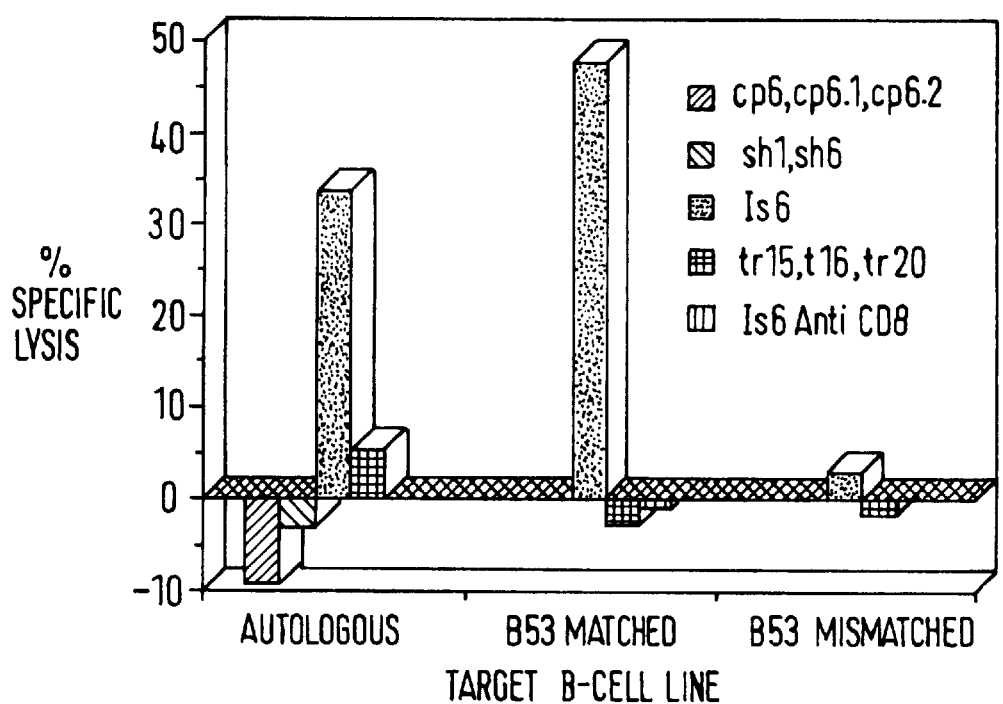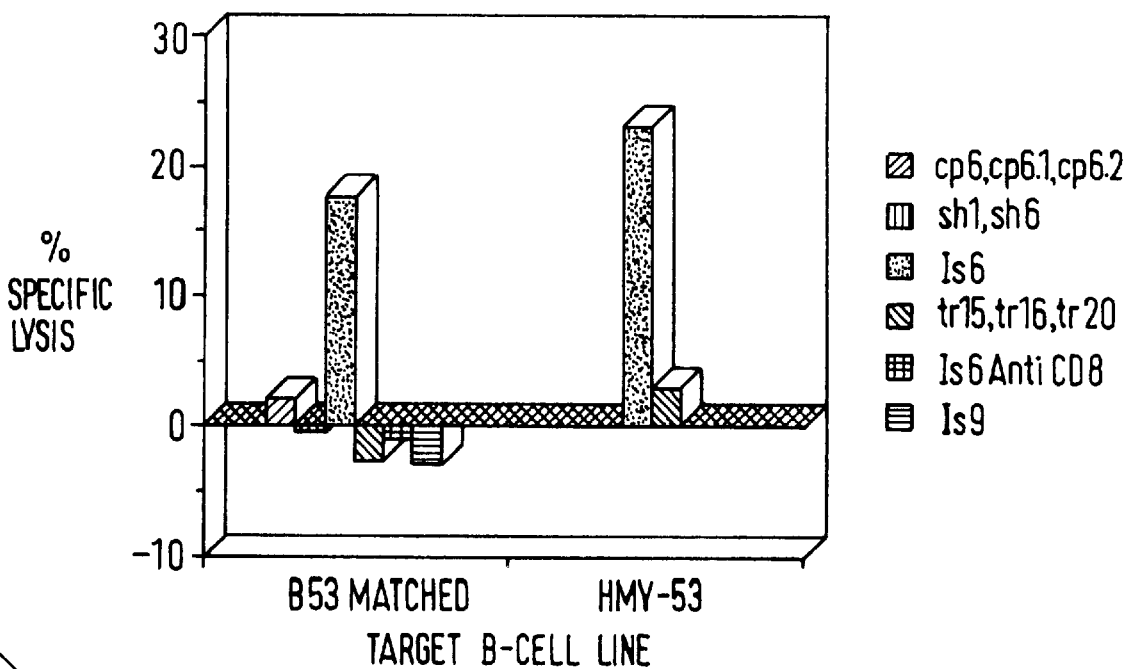
Fig.2.

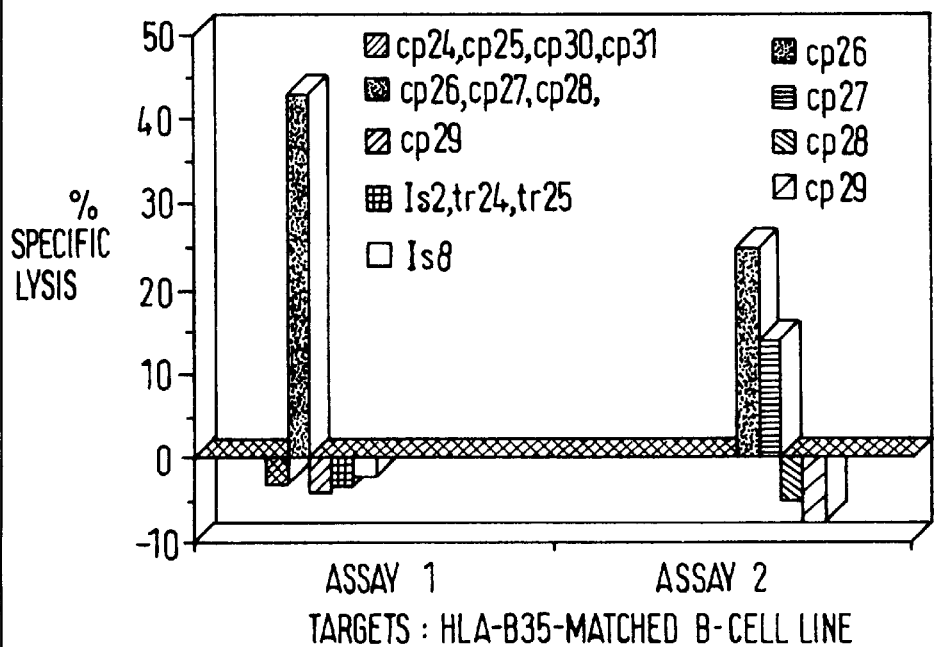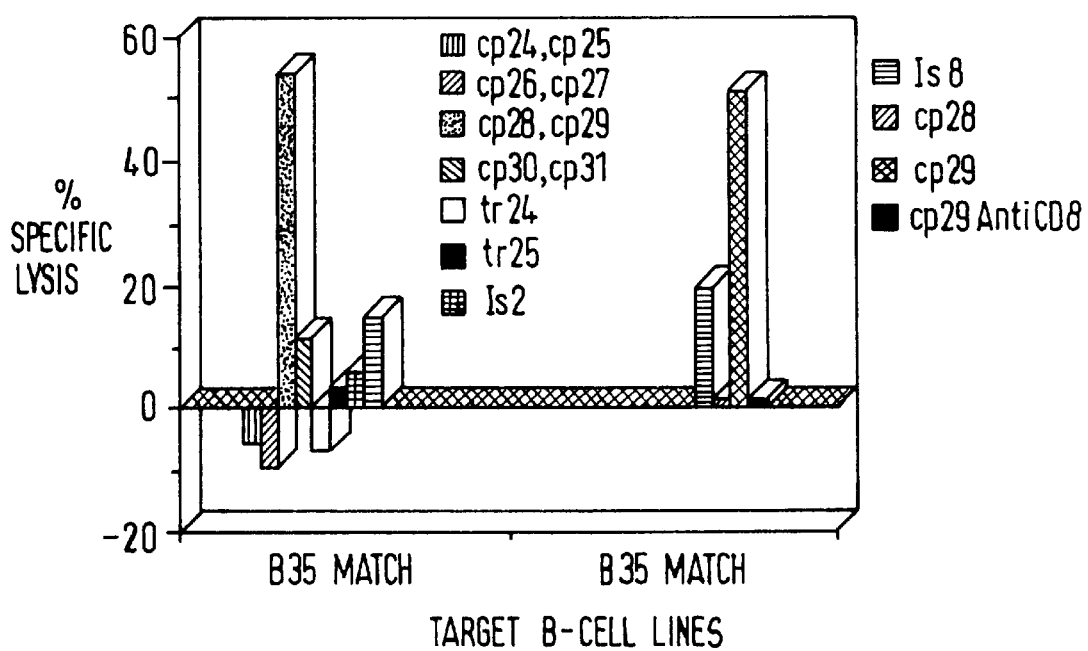
Fig.3.

PLASMODIUM FALCIPARUM MHC CLASS I-RESTRICTED CTL EPITOPES DERIVED FROM PRE-ERYTHROCYTIC STAGE ANTIGENS

BACKGROUND OF THE INVENTION

1. Field of the Invention

Human leucocyte antigens (HLA) play a pivotal role in cellular immune responses. They present peptides derived from various proteins to T lymphocytes: HLA class I molecules present peptides derived from intracellular, cytoplasmic, antigens to (CD8 positive) HLA class I restricted cytotoxic T cells [1], whereas HLA class II molecules present peptides derived from exogenous antigens to (CD4 positive) regulatory T lymphocytes [2].

2. Description of the Related Art

The precise definition of such peptide epitopes is of interest for understanding variation in immune responses between individuals, for identifying the pathogenic mechanisms of autoimmune disorders and for designing subunit vaccines. Recently, by eluting peptides from purified class I molecules, Rammensee and colleagues [3] and others [4] showed that particular HLA class I types bind short peptides of 8–10 amino acids in length. Furthermore, they found conserved amino acids at certain positions in the peptides bound to particular class I molecules which are characteristic of the individual HLA, and thereby defined "motifs" for the type of peptide that binds to a given HLA type. This suggests a means of identifying epitopes within previously known protein antigens by selecting short peptide sequences from that antigen that fit the peptide "motif" for a given HLA. However, it is likely that only a small proportion of peptides fitting such a motif are actually epitopes [5].

We have recently developed a novel assay [6], termed an HLA assembly assay, which provides a means of testing whether particular peptides will bind at high affinity to a particular HLA class I molecule, such as HLA-A2. Peptides which act as epitopes would be expected to bind to their particular class I molecule with high affinity, and we found that known HLA-A2 epitopes did so [6]. This suggested to us that combining the techniques of Rammensee et al. to identify conserved residue(s) in peptides binding a particular HLA class I with the HLA assembly assay to screen such peptides for high-affinity binding, would provide a rapid and novel approach to identifying peptides presented by HLA class I molecules that should include most or all HLA class I restricted T cell epitopes in that antigen. Then cytotoxic T cell assays may be undertaken using lymphocytes from individuals exposed to the micro-organism to identify which of the binding peptides are recognised as cytoxic T cell epitopes.

SUMMARY OF THE INVENTION

Thus the invention provides in one aspect a method of identifying peptides of an antigen of interest which are capable of recognition by or induction of cytotoxic T lymphocytes, which method comprises the steps of:

a) ascertaining a "motif" (at least one particular amino acid at at least one particular position of the peptide) of peptides which bind to a chosen human leucocyte class I antigen,
b) providing peptides having this motif which are present in the (known) sequence of the antigen of interest,
c) screening the provided peptides for recognition by or induction of cytotoxic T lymphocytes.

Step a) involves ascertaining a motif of peptides which bind to the chosen human leucocyte class I antigen. A motif is any feature common to most or all of the peptides sequenced; for example, a particular position of the peptide, e.g. position 2, may be often or always occupied by a particular amino acid. This step may be performed by sequencing peptides derived from the HLA and screening the sequences for a motif. As described below, for HLA-B53 and HLA-B35, proline was found to be predominant at position 2. For other class I molecules different amino acids have been found to be predominant at this position in eluted peptides: arginine in HLA-B27 peptides [22], and leucine or isoleucine in HLA-A2 peptides [3]. The predominance of a single amino acid at position 2 of the peptide in various different HLA types, supports the view that the peptide is anchored in the HLA molecule cleft by high affinity interaction of the sidechain of residue 2 of the peptide with a pocket in the floor of the HLA molecule near to residue 45 of the HLA heavy chain [22].

Step b) involves providing, e.g. by buying or synthesising, peptides which are present in the known sequence of the antigen of interest, and which also have the motif determined in step a). These dual requirements very greatly reduce the number of peptides that need to be provided as representative of the antigen. The peptides are typically 8 to 10 amino acids in length.

Step c) involves screening the provided peptides for recognition by or induction of cytotoxic T lymphocytes (CTL). When the number of peptides involved is large, it is convenient to perform this step in two stages:

c) i) screening the provided peptides to identify those which bind to the chosen HLA. This may conveniently be done by means of the HLA assembly assay [6].
c) ii) screening those peptides which bind to the chosen HLA for recognition by or induction of CTL.

It is necessary for the method that at least part of the sequence of the antigen be known, but the nature of the antigen of interest is not otherwise material to the invention. In the examples below, the antigens of interest are derived from the four pre-erythrocytic stage *P. falciparum* antigens that have been cloned and sequenced; and from a HIV-2 gag protein that has been sequenced. But any other antigen that has been sequenced is susceptible to the same treatment. The antigen of interest may for example be derived from a micro-organism (e.g. bacterium of virus) which causes disease, or may be a self-peptide which generates an auto-reactive immune response in an auto-immune disease.

Examples of specific antigens of interest include the following: any antigen that is expressed in the liver stage of malaria, including CSP, TRAP, Pfs 16, LSA-1, LSA-3 and SALSA; in respect of HIV-1 and HIV-2, the proteins gag, env, nef, and pol; and proteins in Epstein-Barr virus, Cytomegalovirus, Hepatitis-B virus, Hepatitis-C virus and HTLV-1.

The nature of the human leucocyte class I antigen is immaterial to the invention. For any given HLA, it is a straightforward matter to elute bound peptides and sequence them. The HLA is generally one which provides resistance to, or protection from, a disease caused by the antigen of interest. By using this method, we have identified peptides that are expected to be useful in vaccines. These peptides, and vaccines containing them, constitute further aspects of this invention.

Specifically, the invention provides the peptides

| ls6 | K P I V Q Y D N F | (SEQ ID NO: 1) |
|---|---|---|
| ls8 | K P N D K S L Y | (SEQ ID NO: 2) |
| cp26 | K P K D E L D Y | (SEQ ID NO: 3) |
| cp29 | K S K D E L D Y | (SEQ ID NO: 4) |
| sh1 | I P S L A L M L I | (SEQ ID NO: 5) |
| sh6 | M P L E T Q L A I | (SEQ ID NO: 6) |
| cp6 | M P N D P N R N V | (SEQ ID NO: 7) | and conservative variants thereof and longer peptides containing any of these sequences; and vaccines comprising at least one such peptide for immunization against malaria.

In another aspect, the invention provides the peptide

| P1A | T P Y D I N Q M L | (SEQ ID NO: 8) |
|---|---|---| and conservative variants thereof and longer peptides containing any one of these sequences; and vaccines comprising at least one such peptide for immunization against HIV-2.

In yet another aspect, the invention provides use of the *P. falciparum* protein LSA-1 as a CTL-inducing protein for immunization against malaria. The database accession number for LSA-1 is EMBL X56203.

Conservative variants are peptides in which one or possibly more of the stated amino acids has been replaced by another similar amino acid, giving a peptide with similar or identical biological (epitopic) activity. Also included within the scope of the invention are octapeptides obtained by removing a terminal amino acid from a nonapeptide, and longer peptide sequences containing the stated oligopeptides or conservative variants thereof. In vaccines, the oligopeptides are likely to be present in longer sequences.

Titration curve of the assembly of HLA-B53 with varying concentrations of the peptides ls6, cp6, sh6 and α3, YPAEITLYW, which was the major self-peptide eluted from HLA-B53.
(below)

FIG. 2: HLA-B53 restricted CTL. CTL assays using cells from two adult Gambian volunteers with the HLA-B53 antigen, Z 16 (above) and Z 1 (below).

FIG. 3: HLA-B35 restricted CTL. CTL assay results from donor Z 22 (above) and donor Z 87 (below).

Figure 4:
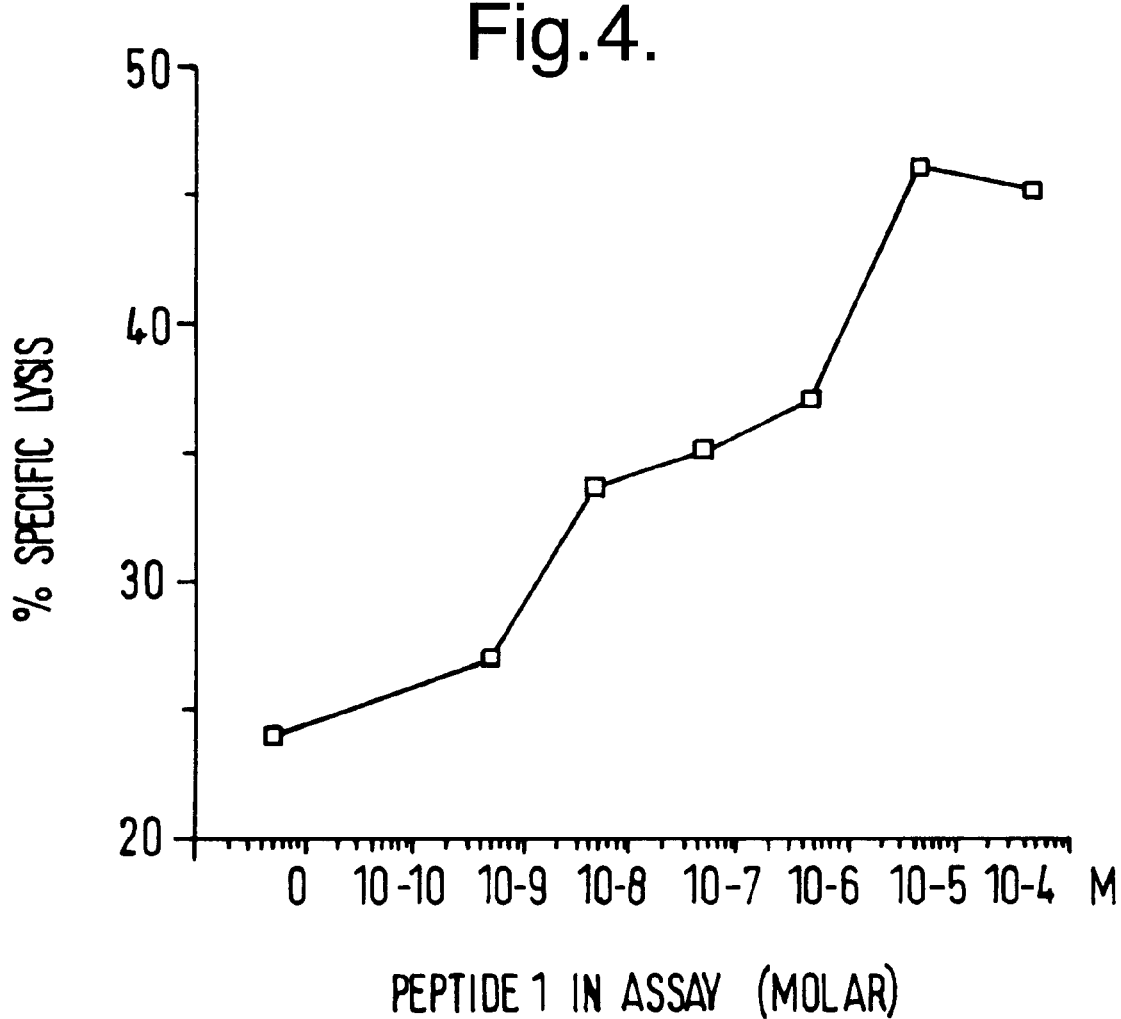

FIG. 4: Peptide concentration titration for CTL specific for the HIV-2 gag peptide, P1.

DETAILED DESCRIPTION OF THE INVENTION

Much progress has been made in the past decade in understanding the immunology of HIV-1, although far less is known about HIV-2. The latter was first described in 1986 in West Africa, and is related to HIV-1, the prototype human immunodeficiency virus. Similarities between the two viruses include tropism for cells bearing the CD4 marker, although HIV-2 has a lower binding affinity for the CD4 receptor than HIV-1, major antigenic cross reactivity and similar genome structure with nucleotype homology.

In order that the important differences between HIV-1 and HIV-2 might be more completely understood, and that vaccines which stimulate both cellular and humoral immune reactions may be developed for both retroviruses, we have carried out a study of CTL activity in patients infected with HIV-2 in the Gambia. As described below, we have used the method of this invention as a strategy for providing peptide epitopes in an HIV-2 gag protein.

Firstly, we report the application of this strategy to identifying epitopes in pre-erythrocytic stage antigens of *Plasmodium falciparum*, the causative agent of the most severe malaria of humans. We have found that in African children, the HLA class I antigen. HLA-B53, is associated with protection from severe malaria, and have proposed that this results form the ability of this antigen to elicit a protective cytotoxic lymphocyte response targetted at the liver-stage of the parasite's life cycle[7]. The antigen and epitope against which such a CTL response may be directed was previously unknown. By eluting self-peptides from HLA-B53 we identified a sequence motif for bound peptides and have synthesized sixty octamer, nonamer or decamer peptides bearing this motif from the four pre-erythrocytic stage *P. falciparum* antigens that have been cloned and sequenced[8-13]: each of these antigens has been used in or is currently awaiting human vaccine trials. One or more peptides from each antigen bound to HLA-B53 in the HLA assembly (binding) assay[6] and these were tested further using lymphocytes from Africans naturally exposed to malaria. None of the peptides from the three sporozoite antigens, which have been the focus of most previous work[8-11,14-21], elicited CTL responses. However, a nonamer peptide from liver-stage specific antigen-1 (LSA-1)[12,13] elicited secondary CTL responses in HLA-B53 positive individuals and sequence analysis showed this to be a conserved epitope in the local parasite population. In contrast, a similar approach for the HLA-B35 molecule identified responses mainly to polymorphic epitopes, variants of which escape CTL recognition. These results suggest a possible molecular basis for the association of HLA-B53 with resistance to severe malaria, and identify LSA-1 as an important antigen for attempts to induce CTL-mediated immunity to this infectious disease.

RESULTS

Peptide Elutions

Self peptides were acid eluted[3] from HLA-B53 (HLA-B*5301), separated by HPLC and sequenced. The pool sequence (Table 1) showed a predominant signal for proline at position 2 indicating that most peptides bound to HLA-B53 have this "anchor" residue at position 2. A similar approach was taken for HLA-B35 (HLA-B*3501), which was not significantly associated with altered resistance to severe malaria in the Gambian case-control study of malaria susceptibility[7]. HLA-B35 also showed a strong preference for proline at position 2 of bound peptides (Table 1), probably because of its sequence identity to HLA-B53 in the region of the B pocket[22] of the molecule. However, HLA-B35 showed a predominant tyrosine residue at position 9 of bound peptides: no anchor residue was identified at this position for HLA-B53.

These peptide motifs allowed us to search the sequences of known *P. falciparum* antigens for potential epitopes for HLA-B53 and -B35. We reasoned that a malaria antigen (or antigens) which could interact with HLA-B53 and account for the disease association should be expressed early in the liver-stage of the parasite's life cycle: human erythrocytes do not express class I molecules[23], and enhanced CTL lysis of macrophages which have engulfed blood stage parasites is unlikely to benefit the host. Furthermore, comparison of radiation doses required to induce protection in the irradiated sporozoite model of pre-erythrocytic immunity has indicated that antigens expressed early in development in the liver are of most importance for protection[24-26]. So, peptides conforming to these motifs were identified in the three sequenced sporozoite antigens (CSP, TRAP and Pfs16) and the only sequenced liver-stage specific antigen (LSA-1) from *P. falciparum*.

HLA Assembly Assay

A total of 60 peptides with proline at position 2 were synthesized (Table 2), to determine whether these were HLA-B53 restricted CTL epitopes in malaria-immune Africans. However, this large number of peptides would have prevented comparison of responses to all peptides in the same individual, unless very large blood volumes were donated. So, we first used an HLA assembly assay[6] to identify a subgroup of these peptides which bound with high affinity to HLA-B53. Only eight peptides from the four malaria antigens bound in this assay, all of which had hydrophobic or aromatic residues at position 9 (Table 2, FIG. 1). For HLA-B35 peptides, the additional requirement for a terminal tyrosine limited the number of potential epitopes to be tested to ten (Table 2).

HLA-B53 Restricted CTL to *P. falciparum*

Most adults in areas of hyperendemic malaria have immunity to malaria which, although not completely effective in preventing parasitaemia and occasional symptomatic episodes, is strongly protective against life-threatening malaria[27]. We studied healthy adult Gambian villagers with the HLA-B53 antigen. CTL were detected to none of the peptides from the three sporozoite antigens, but three out of six individuals tested responded to the ls6 peptide from LSA-1 (FIG. 2). This CTL lysis was HLA-B53 restricted, peptide-specific and inhibitable by anti-CD8 antibodies. We then sequenced parasite DNA from nine Gambian isolates (FIG. 2, legend): in each, the ls6 epitope was identical to the published sequence[13], indicating that it is largely or completely conserved in this population.

HLA-B35 Epitope Variants in *P. falciparum*

Eight Gambians with the HLA-B35 antigen were tested using the peptides synthesised to match the HLA-B35 motif (Table 2), and in two individuals CTL were identified. One recognised an epitope from CSP, cp26 (FIG. 3), that represents the 8 amino-terminal residues of the 23-mer peptide previously shown to elicit CTL in 3 volunteers immunised with irradiated sporozoites[17]. In the two volunteers reported to have HLA-B35 this octamer is likely to have been the minimal epitope. Importantly, however, CTL from the Gambian that recognised cp26, did not recognise two other naturally occurring variants of this epitope, cp28 and cp29, and showed only limited recognition of another variant cp27. Conversely, the second Gambian responder recognised the uncommon variant, cp29, but did not recognise cp26, cp27 nor cp28 (FIG. 3). This individual also had CTL specific for an octamer peptide, ls8, from LSA-1.

Identification of a CTL Epitope in HIV 2

Although high numbers of HIV 1 specific CTL have been demonstrated in infected asymptomatic individuals (e.g. ref. 28) the CTL response to HIV2 has not been studies in humans. HIV-2 positive adult Gambians were identified and their peripheral blood lymphocytes restimulated as described in FIG. 4. A clear CTL response was observed in three out of three individuals tested using a HLA-B53 matched target B cell line infected with a vaccinia virus recombinant containing the gag gene of HIV2. Inspection of the amino acid sequence of this protein[29] revealed two sequences conforming to the HLA-B53 peptide binding motif, as now defined by the sequencing of eluted peptides and the malaria peptide assembly assay data: i.e. proline at position two and a hydrophobic amino acid at position nine. Synthetic peptides of 20 amino acids in length containing these two potential epitopes ALSEGCTPYDIN-QMLNNCVGD (SEQ ID NO:9) designated P1 and HLPL-SPRTLNAWVKLIEEKK (SEQ ID NO:10), designated P2) were tested in the HLA-B53 assembly assay. P1 and the nonamer peptide TPYDINQML (SEQ ID NO: 8), designated P1A, gave a positive result in the assemble assay but P2 did not. All three of these peptides were tested for recognition with HIV 2-gag restimulated CTL from one Gambian individual, and these CTL recognised targets pulsed with P1. P1A but not the P2 peptide. When the P1A peptide was tested at various concentrations in a CTL assay (FIG. 4) it could sensitise target B cells for lysis at a concentration as low as $10^{-8}$M.

Discussion

Using a novel combination of sequencing of peptides eluted from an HLA class I allele and screening of peptides consistent with this "motif" (here a proline at position 2 of the peptide) in an HLA assembly assay we have been able to identify peptides which are strong candidates for eliciting protective CTL responses in humans, and have gone on to show that one of these, ls6, is recognised by cytotoxic T lymphocytes of Gambians naturally exposed to *P. falciparum* malaria. To identify HLA-B35-restricted CTL we have modified this approach to omit the HLA assembly assay step and screened all peptides conforming to the HLA-B35 motif for CTL responses, identifying further epitopes. The identification of CTL to several epitopes in *P. falciparum* antigens indicates that natural exposure to malaria leads to processing of pre-erythrocytic antigens for HLA class I presentation. CTL recognising the conserved ls6 epitope of LSA-1 are restricted through HLA-B53 and, although further work is required to demonstrate CTL in young children and to show that, as in rodent models[16,20,21], human CTL can kill intra-hepatic parasites, the findings support our proposal[5] that the association of this HLA class I antigen with resistance to severe malaria may be mediated by CTL. Our association of HLA-B53 with malaria resistance and the observation that HLA-B53 restricted CTL recognize only LSA-1 of several major pre-erythrocytic antigens from *P. falciparum*, constitute a genetic approach to implicating this antigen (LSA-1) in providing protective immunity to malaria. LSA-1 is here shown to be a target of natural, and by implication from the case-control study protective, CTL responses, and this indicates that CTL-inducing vaccines using part, parts or all of this antigen should be useful in prophylaxis against *P. falciparum* malaria.

We propose that a straightforward extension of this approach should allow rapid detection of potential class I restricted peptides from other microorganisms, and have demonstrated this by identification of a CTL epitope restricted by HLA-B53 in the gag protein of HIV-2. A natural and straightforward extension of this "reverse immunogenetic" approach would be to search for self-peptides which may be targets of autoreactive immune responses in various autoimmune disease. This new approach should considerably facilitate the search for HLA class I restricted epitopes by reduce the amount of time required to analyze a smaller number of peptides as well allowing substantial cost savings by reducing the number and size of peptides that need to be synthesized.

REFERENCES

1. Bodmer H and Townsend ARM Annual Review of Immunology 7: 601–24 (1989).
2. Rudensky AY et al. *Nature* 353: 622–7 (1991).
3. Falk, K., Rotzscke, O., Stevanovic, S., Jung , G. & Rammensee, H. *Nature* 351,290–296 (1991).
4. Jardetsky, T. S., Lane, W. S., Robinson, R. A., Madden, D. R. & Wiley, D. C. *Nature* 353, 326–329 (1991).
5. Pamer, E. G., Harty, J. T. & Bevan M. J. *Nature* 353, 852–855 (1991).

6. Elvin, J., Cerundolo, V., Elliot, T. & Townsend, A. *Eur. J. Immunol*, 12025–2031 (1991).
7. Hill, A. V. S. et al. *Nature* 352, 595–600 (1991).
8. Dame, J. B. et al. *Science* 225, 593–599 (1984).
9. Robson, K. J. H. et al. *Nature* 335, 79–82 (1988).
10. Cowan, G., Krishna, S., Crisanti, A. & Robson, K. J. H. *Lancet* 339, 1412–1413 (1992).
11. Moelans, I. I. M. D., Meis, J. F. G. M., Kocken, C., Konings, R. N. H. & Schoenmakers, J. G. G. *Mol. Biochem. Parasitol.* 45, 193–204 (1991).
12. Guerin-Marchand, C. et al. *Nature* 329, 164–167 (1987).
13. Zhu, J. & Hollingdale, M. *Mol. Biochem. Parasitol.* 48, 223–226 (1991).
14. Kumar, S. et al. *Nature* 334, 258–260 (1988).
15. Romero, P., Maryanski, J. L., Corradin, G., Nussenzweig, R. S. & Nussenzweig V. *Nature* 341, 323–326 (1989).
16. Hoffman, S. L. et al. *Science* 244, 1078–1081 (1989).
17. Malik, A., Egan, J. E., Houghten, R. A., Sadoff, J. C. & Hoffmann, S. L. *Proc. Natl. Acad. Sci. U.S.A.* 88, 3300–3304 (1991).
18. Doolan, D. L., Houghten, R. A. & Good, M. F. *Int. Immunol.* 3, 511–516 (1991).
19. Sedegah, M. et al. *J. Immunol.* 149, 966–971 (1992).
20. Weiss, W. R. et al. *J. Exp. Med.* 171, 1083–1090 (1990).
21. Rodrigues, M. M. et al. *Int. Immunol.* 3, 579–585 (1991)
22. Madden, D. R., Gorga, J. C., Strominger, J. L. & Wiley, D. C. *Nature* 353, 321–325 (1991).
23. Harris, R. & Zervas, J. D. *Nature* 221, 1062–1063 (1969).
24. Druihle, P. & Marchand, C. in McAdam, K. P. W. J. ed., *New Strategies* in Parasitology, Churchill-Livingstone, Edinburgh, pp 39–48 (1989).
25. Mellouk, S., Lunel, F., Sedegah, M., Beaudoin, R.-L. & Druihle, P. *Lancet* 335, 721 (1990).
26. Suhrbier, A., Winger, L. A., Castellano, E. & Sinden, R. E. *Infect. Immun.* 58, 2834–2839 (1990).
27. McGregor, I. A. & Wilson, R. J. M. In: *Malaria: principles and practice of malariology*. Churchill Livingstone, Edinburgh, pp 559–620 (1988).
28. Gotch, F. et al. International Immunology 7, 707–717 (1990).
29. Myers G. et al. (eds) Human retroviruses and AIDS 1992: a compilation and analysis of nucleic acid and amino acid sequences. Los Alamos National Laboratory, New Mexico, USA (1992).
30. Allsopp, C. E. M. et al. *Hum. Immunol.* 30, 105–109 (1991).
31. Hayashi, H. et al. *Immunogenetics* 32, 195–199 (1990).
32. Sutton, J. et al. *Eur. J. Immunol.* In Press (1993).
33. Yamamoto, J., Kariyone, A., Akiyama, N., Kano, K. & Takiguchi, M. *Proc. Natl. Acad. Sci. U.S.A.* 87, 2583–2587 (1990).
34. Barnstable C. J. et al. *Cell* 14, 9–20 (1978).
35. Doolan, D. L., Saul, A. J. & Good, M. F. *Infect. Immunity* 60, 675–682 (1992).
36. Townsend, A. et al. *Cell* 62, 285–295 (1990).
37. Schumacher, T. N. M. et al. *Cell* 62, 563–567 (1990).
38. Cerundolo, V. et al. *Nature* 345, 449–456 (1990).
39. Elvin, J. et al. *J. Immunol.* Methods In Press (1992)
40. Van Bleek, G. M & Nathenson S. G. *Nature* 348, 213–216 (1990).
41. Ellis, S. et al. *Hum. Immunol.* 13, 13–20 (1985).
42. Bodmer, H. C., Gotch, F. M. & McMichael, A. J. *Nature* 337, 653–655 (1989).
43. Conway, D., Greenwood, B. M. & McBride, J. S. *Parasitology* 103, 1–6 (1991).
44. Pircher, H. P. et al. *Nature* 346, 629–633 (1990).
45. Phillips R. E. et al. *Nature* 354, 453–459 (1991).
46. Lockyer, M. J., Marsh, K. & Newbold, C.I. *Mol. Biochem. Parasitol.* 37, 275–280 (1989).
47. Nixon, D. F. et al. *Nature* 336, 484–487 (1988).

| HLA-B53 Pool Sequence | | | | | | | | | |
|---|---|---|---|---|---|---|---|---|---|
| | 1 | 2 | 3 | 4 | 5 | 6 | 7 | 8 | 9 |
| Anchor | | P | | | | | | | |
| Strong | | | | | E | I | | | |
| Weak | | | | S | F | I | L | Y | |
| | | | | Y | | K | L | | |
| | | | | F | | N | Q | | |
| | | | | M | | Q | | | |

| HLA-B35 Pool Sequence | | | | | | | | | |
|---|---|---|---|---|---|---|---|---|---|
| | 1 | 2 | 3 | 4 | 5 | 6 | 7 | 8 | 9 |
| Anchor | | P | | | | | | | Y |
| Strong | | | | F | | | | | |
| Weak | | | | F | E | E | | | |
| | | | | Y | I | K | | | |
| | | | | L | N | | | | |
| | | | | M | Q | | | | |
| | | | | | Y | | | | |

Table 1

Pool sequences of eluted peptides from HLA-B53 (above) and HLA-B35 (below). The sequences of these HLA molecules differ from each other at only five amino acids, all in the α1 domain at the end of the cleft which binds the carboxy-terminus of the peptide[30,31]. Anchor, strong and weak signals are classified as described by Falk et al.[3]. Peptides from both molecules have proline as an anchor residue at position 2, but only HLA-B35 has a clear anchor, tyrosine, at position 9. Partial sequences of several individual peptide peaks eluted from HLA-B53 (not shown) and a single complete sequence from the largest individual peak, YPAEITLYW (SEQ ID NO:11), all showed proline at position 2. The latter sequence was identified as part of the α3 domain sequence of HLA-B53, as well as some other class I molecules.

In contrast, peptides eluted by the same method from a HLA-B8 transfectant showed anchor residues at positions 3 and 5[32].

Methods

To determine whether particular sequences features were found in peptides presented by HLA-B53 (HLA-B*5301), as has been described for other class I molecules[3,4], we used the cell line Hmy-B53[33]: this was derived by transfection of the cell line CIR, which lacks HLA-A and -B molecules, with a genomic clone of HLA-B53.1.5×10[10] Hmy-B53 or Hmy-B35 cells[33] were pelleted and lysed and HLA class I molecules purified with the monoclonal antibody W6/32[34] on an immunoaffinity column as described[3]. Following acid elutions in 0.1% TFA, the supernatants were dried by vacuum centrifugation and separated by reversed-phase HPLC using a Brownlee Aquapore RP300 column (C8, 100×2 mm) and Severn Analytical equipment. Peptide peaks[3] were pooled and sequenced using an Applied Biosystems 473A protein sequencer and Applied Biosystems model 610 data analysis software.

| | HLA-B53 Peptides | | | | |
|---|---|---|---|---|---|
| | 1 2 3 4 5 6 7 8 9 10 | pos. | | 1 2 3 4 5 6 7 8 9 10 | pos. |
| cp1 | N P N A N P N A | 150 | ls1 | I P A I E L P S E | 1658 |
| cp2 | N P N A N P N A N | 150 | ls2 | L P S E N E R G Y | 1663 |
| cp3 | K P K H K K L K Q | 107 | ls3 | I P H Q S S L P Q | 1673 |
| cp4 | N P G D G N P D P G | 115 | ls4 | L P Q D N R G N S | 1679 |
| cp5 | N P D P N A N P N | 120 | ls5 | K P E Q K E D K S | 1728 |
| cp6 | (7) M P N D P N R N V | 300 | ls6 | (1) K P I V Q Y D N F | 1786 |
| cp7 | D P N R N V D G N | 303 | ls7 | K P N D K S L Y D | 1850 |
| cp8 | S P C S V T C G N | 347 | ls9 | K P I V Q Y D N | 1786 |
| cp9 | K P G S A N K P K | 362 | | | |
| cp10 | K P K D E L D Y E | 368 | | | |
| cp11 | E P S D K H I E Q | 325 | | | |
| cp12 | E P S D Q H I E K | 325 | tr1 | S P C S V T C G K | 251 |
| cp13 | E P S D K H I K E | 325 | tr2 | K P N I P E D S E K | 361 |
| cp14 | E P S D K H I E K | 325 | tr3 | I P Y S P L P P K | 413 |
| cp15 | K P G S A D K P K | 362 | tr4 | E P S P N P E E G K | 327 |
| cp16 | K P K D Q L D Y A | 368 | tr5 | H P E R E E H E K | 473 |
| cp17 | K P K D E L D Y A | 368 | tr6 | N P E N P P N P D I | 348 |
| cp18 | K P K D Q L D Y E | 368 | tr7 | V P K N P E D D R | 376 |
| cp19 | K P K D Q L D Y | 368 | tr8 | P P K V L D N E R | 419 |
| cp20 | E P S D Q H I E | 325 | tr9 | V P N S E D R E T R | 443 |
| cp21 | N P D P N A N P N V | 120 | tr10 | R P H G R N N E N R | 452 |
| cp22 | N P N V D P N A N | 126 | tr11 | E P E D D Q P R P R | 297 |
| cp23 | D P N A N P N V D | 130 | tr12 | L P P K V L D N E R | 418 |
| cp6.1 | M P N Y P N R N V | 300 | tr13 | I P D S I Q D S L | 164 |
| cp6.2 | M P N N P N R N V | 300 | tr14 | I P E D S E K E V | 364 |
| | | | tr15 | E P A P F D E T L | 529 |
| sh1 | (5) I P S L A L M L I | 7 | tr16 | V P D E P E D D Q | 295 |
| sh2 | K P A G K G S P S | 33 | tr18 | I P K K P E N K H | 390 |
| sh3 | S P S T L Q T P G | 39 | tr19 | T P K H P E R E E | 470 |
| sh4 | T P G S S S G A S | 45 | tr20 | H P S D G K C N L | 206 |
| sh5 | G P N Q G G L S Q | 58 | tr21 | G P F M K A V C V | 228 |
| sh6 | (6) M P L E T Q L A I | 77 | tr22 | P P K W E P L D V | 287 |

| | HLA-B35 Peptides | | | | |
|---|---|---|---|---|---|
| | 1 2 3 4 5 6 7 8 9 10 | pos. | | 1 2 3 4 5 6 7 8 9 10 | pos. |
| cp26 | K P K D E L D Y | 368 | ls2 | L P S E N E R G Y | 1663 |
| cp27 | K P K D Q L D Y | 368 | ls8 | (2) K P N D K S L Y | 1850 |
| cp28 | K P K D Q L N Y | 368 | | | |
| cp29 | K S K D E L D Y | 368 | tr24 | H P S D G K C N L Y | 206 |

-continued

| | | | | | | | | | | | | | | | |
|---|---|---|---|---|---|---|---|---|---|---|---|---|---|---|---|
| cp30 | E | P | S | D | K | H | I | E | Q | Y | 325 | tr25 | V P G A A T P Y | 519 |
| cp31 | E | P | S | D | Q | H | I | E | K | Y | 325 | | | |

Note - Numbers in brackets adjacent to the amino acid sequences represent SEQ ID NO's for those amino acid sequences listed in the attached Sequence Listing.

Table 2

*P. falciparum* peptides. Antigens studied Peptides were identified in the four sequenced pre-erythrocytic antigens of *P. falciparum*: (i) circumsporozoite protein[8] (CSP), a 412 amino acid sporozoite protein; (ii) thrombospondin-related anonymous protein[9] (TRAP), 559 amino acids and expressed by sporozoites[10] and blood-stage parasites; (iii) liver-stage specific antigen-1[12,13], 1909 amino acids and expressed only by the liver-stage parasite; and (iv) sporozoite hepatocyte binding antigen[11] (SHEBA or Pfs16), 157 amino acids and found in both sporozoites and gametocytes. Antigens expressed by sporozoites will also be present during the early phase of hepatocyte development. CSP and LSA-1 have large central repeats spanning 164 and 1475 amino acids, respectively[8,13].

above Peptides synthesized and tested in the HLA assembly assay for binding to HLA-B53. Peptides shown to bind to HLA-B53 are highlighted in bold type. The amino acid sequence, using the single letter amino acid code, and the number of the amino-terminal residue in the published sequence[8,9,11,13] is shown. The CSP, LSA-1, TRAP and SHEBA antigens are indicated by the prefixes cp, ls, tr and sh, respectively. All possible nonamer peptides with proline at position 2 were synthesized for CSP, LSA-1 and SHEBA; where a sequence had been shown to be polymorphic variant peptides, e.g. cp10, cp16-18, were also synthesized. The peptides from CSP which bound to HLA-B53, i.e. cp6, cp6.1, and cp6.2 are allelic variants[35]. Additionally, some octamer and decamer peptides were analyzed but none of these bound. The decamer, cp4, was made with an added terminal glycine to facilitate synthesis. Inspection of the sequences of peptides binding to HLA-B53 indicated that several branched aliphatic or aromatic residues, but not polar or hydrophilic residues, can be accommodated at the carboxy-terminus. So, for TRAP, which has a total of 48 prolines a subset of 21 of these, including all possible peptides with proline at position 2 and carboxy-termini of residues, V, A, L, I, F or W were synthesized. The cell line T2-B53 has endogenous HLA-A2 and HLA-B51 genes as well as the transfected HLA-B53 gene. HLA-B51, as well as HLA-B53, is immunoprecipitated by the antibodies used, so data on peptide binding to this HLA type was obtained in the same experiments: only peptides sh1, sh6 and cp6, but not cp6.1 nor cp6.2, bound to HLA-B51. All the highlighted peptides as well as the eluted self peptide YPAEITLTW (SEQ ID NO:74), and the HIV-2 HLA-B53 epitope, TPY-DINQML (SEQ ID NO: 8) were found to show 50% maximum binding to HLA-B53 in the micromolar range (2–6 $\mu$M) (FIG. 1).

below Peptides synthesized to match the HLA-B35 motif. Only a single nonamer peptide in the four pre-erythrocytic antigens, ls2, has proline at position 2 and tyrosine at position 9. So, all possible peptides with proline at 2 and tyrosine at 8 or 10, as well as their allelic variants, were also tested. In addition to the 10 peptides shown two longer peptides, cp24 and cp 25, ENDIEKKICKMEKCS (SEQ ID NO:75) and ELDYANDIEKKICKM (SEQ ID NO: 76), were also included in CTL assays: these, with cp26 overlap the 23-mer sequence previously shown to contain a CTL epitope[14]. Peptides shown to be epitopes (FIG. 3) are highlighted in bold type.

Figure Legends

Figure 1:
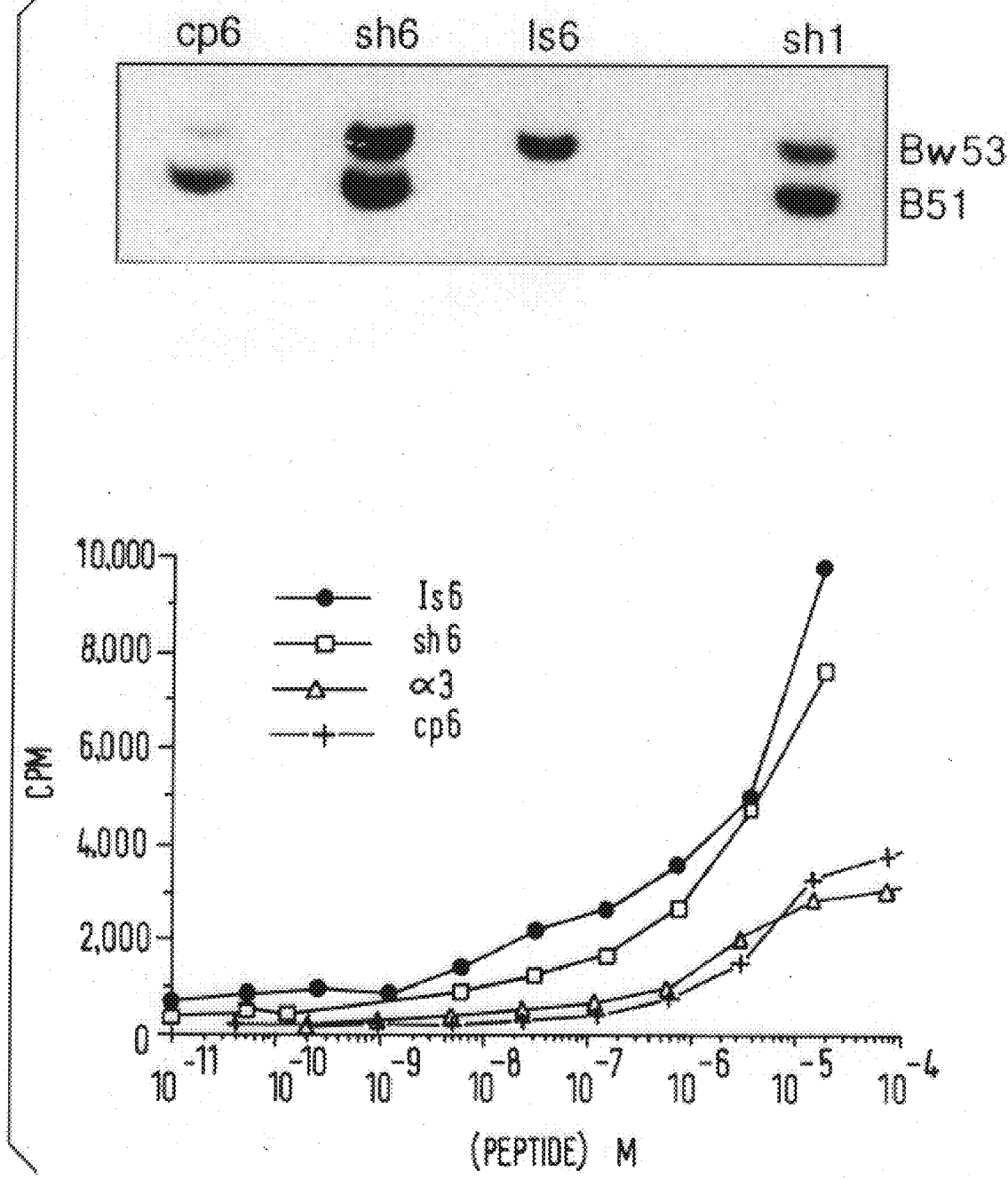
FIG. 1: Autoradiograph of a one-dimensional isoelectric focusing gel analysis showing binding or stabilization of HLA-B53 and -B51 by peptides cp6, sh1 and sh6, and of HLA-B53 by the ls6 peptide (above).

FIG. 1 HLA assembly assay. Stable assembly of HLA class I molecules in the mutant cell line T2 has been found to be dependent on binding by peptides[36-38] and this phenomenon can be used as a peptide binding assay[6]. We have found, using this assay, that all optimised CTL epitopes for other class I molecules (HLA-A2, $D^b$ and $K^b$) have bound with high affinity, and the assay has recently been used to identify a HIV-gag CTL epitope in mice by screening of potential epitopes fitting the $D^b$ motif[39].

above Autoradiograph of a one-dimensional isoelectric focusing gel analysis showing binding or stabilization of HLA-B53 and -B51 by peptides cp6, sh1 and sh6, and of HLA-B53 by the ls6 peptide. Peptide binding is associated with stabilisation of assembled class I molecules which appear as strong bands in the autoradiograph. In the absence of peptide (lane 2) class I molecules lose conformation, dissociate and are not precipitated by specific monoclonal antibodies. The peptides tested were, from left: cp6, saline negative control, sh6, ls7, ls6, sh5, cp22, sh1. Cp6 bound more strongly to HLA-B51 than to HLA-B53 but the allelic variants of this peptide with single amino acid substitutions at position 4, cp6.1 and cp6.2; bound more strongly to HLA-B53 and very poorly to HLA-B51 (data not shown).

below Titration curve of the assembly of HLA-B53 with varying concentrations of the peptides ls6, cp6, sh6 and $\alpha$3, YPAEITLYW (SEQ ID NO:11), which was the major self-peptide eluted from HLA-B53. The Y axis represents the quantity of assembled class I heavy chain precipitated after addition of peptide, the X axis the concentration of peptide added. The ls6 and sh6 peptides and the cp6 and $\alpha$3 peptides were titrated in separate experiments. All four show 50% of maximum assembly of HLA-B53 in the micromolar concentration range ($10^{-5}$–$10^{-6}$M), as does the HIV-2 nonamer epitope for HLA-B53. This is a higher concentration range than for HLA-A2-binding epitopes and some HLA-B51-binding peptides, but comparable to an epitope[40] for the mouse $K^b$ molecule (ref 39 and unpublished data).

Methods

The assembly assay was performed as described elsewhere[6,36,38,39]. Briefly, the mutant cell line T2-B53 was derived from T2 cells of HLA type, HLA-A2, -B51, by transfection with a genomic clone of HLA-B53 using hygromycin selection. Peptides were synthesized by Cambridge Research Biochemicals, Cheshire, UK using their multiple peptide synthesis service or, subsequently, in Oxford using the same procedure and apparatus. Peptide concentrations were determined with a Micro BCA colourimetric assay (Pierce). Peptides were added to lysates of $^{35}$S-methionine-labelled cells and incubated overnight at 4° C.[36]. Stable assembled class I molecules were then precipitated with monoclonal antibodies W6/32[34] (reactive with all assembled class I molecules) or MHM5[41] (reactive with assembled HLA-B but not HLA-A molecules). The precipitated class I molecules were separated by one dimensional iso-electric focusing, visualised by autoradiography and quantified as described[6,39]. All peptides were initially tested at 4 μM concentration, and those found to bind titrated to estimate binding affinities.

FIG. 2 HLA-B53 restricted CTL. CTL assays using cells from two adult Gambian volunteers with the HLA-B53 antigen, Z 16 above and Z 1 below. Both showed cytolytic activity towards B lymphoblastoid cell lines (BCL) with HLA-B53 when incubated with the ls6 peptide, but not when incubated with the peptides that bound to HLA-B53 from the other three pre-erythrocytic antigens. The cytolytic activity was HLA-B53-restricted and peptide specific. Ls9, the octamer peptide derived from ls6 by removing the carboxy-terminal residue was not recognised: ls9 did not bind to HLA-B53 in the assembly assay (Table 2). The B53 matched cell lines were matched to the donors only for HLA-B53; the B53 mismatched line was matched to Z 16 (HLA type A3, A19, B35, B53, Cw3, Cw6) only for HLA-Cw3. The Hmy-B53 line expresses, in significant amounts, only HLA-B53 and -Cw4. CTL activity was inhibitable by an anti-CD8 monoclonal antibody, M236, a gift from RW Knowles (Sloane-Kettering, New York) and CTL lines could be maintained by weekly restimulation with peptide-pulsed irradiated autologous B cell lines. One further volunteer from Brefet, out of six HLA-B53 positive individuals tested, showed HLA-B53 restricted CTL responses to the ls6 peptide but none recognised any peptide from the other three antigens. Further samples of blood were obtained after 2–3 weeks from donors Z 16 and Z 1. On this occasion, CTL to ls6 were again grown from Z 1 but not from Z 16. Two caucasian Oxford residents with HLA-B53 but not exposed to malaria were tested as controls and neither responded to any peptide.

HLA-B53 positive individuals from the conurbation around the capital Banjul, where malaria transmission is 10–100 times less intense, were also tested. In only one of nine such volunteers could CTL be grown, again only to the ls6 peptide, suggesting that CTL may be more readily detectable in areas of higher malaria transmission.

To determine whether the ls6 epitope is conserved or significantly variable amongst *P. falciparum* isolates in The Gambia, DNA extracted from samples collected from nine children with acute malaria[5] was examined. A segment of the LSA-1 gene containing the DNA encoding this epitope was amplified by PCR and sequenced directly. In all nine samples the previously reported[13] 27 bp sequence was found.

Methods

Volunteers from the Gambian village, Brefet, which has hyperendemic malaria, were studied at the time of year with lowest malaria transmission: none had had a recent febrile illness. Peripheral blood lymphocytes were separated from whole blood and incubated at $3\times10^6$ cells per well of a 24 well Costar plate. The cells were stimulated with peptides that had bound to HLA-B53 in the HLA assembly assay, each at 25 μM, pooled as follows: cp6, cp6.1, cp6.2, sh1, sh6; and ls6, tr15, tr16 and tr20. The tr16 peptide was included as a non-binding control. At 72 hours 10 U ml$^{-1}$ IL-2 (Cetus) was added and CTL assays were performed on day 8. $^{51}$Cr labelled BCL were preincubated for 1 hr with 25 μM of one or more peptides, and without peptide, and a 4 hr assay performed as described[42]. Assays (shown here and in FIG. 3) were performed at effector to target cell ratios of 50:1 and 8:1 but only the results of the former are shown: lysis at the lower ratio was invariably much lower. CTL lysis of target cells was also detectable without peptide preincubation, by adding the ls6 peptide into the CTL assay at $10^{-7}$M (not shown). Background chromium release was from 15–20%. Non-specific lysis, possibly due to NK-like cells, was higher in Gambians than in Europeans, typically 15–25%. Specific lysis was calculated by the standard formula[42] and values in the absence of peptide subtracted to yield the values shown. CTL could also be generated by restimulation with the ls6 peptide without tr15, tr16 and tr20 in the medium (not shown). CTL lines were maintained by weekly restimulation with equal numbers of irradiated autologous peptide-pulsed BCL. HLA typing was performed by both serological and PCR-based methods as described .

The LSA-1 gene was amplified for 35 cycles from nt 5372 to nt 5701[13] using the primers GTGCTGAATATGACGAT-TCA (SEQ ID NO:77) and CCTTTTCCTTATTAACCTGC (SEQ ID NO:78), in a buffer with 1 mM MgCl and 10% DMSO, with annealing at 55° C. The purified amplification products were directly sequenced using a ΔTaq cycle-sequencing kit (US Biochemical) and the manufacturers' protocol. Briefly, the reverse strand primer TTCCT-TCATCTAAATCATCT (SEQ ID NO:79) (0.5 pmol) was labelled with $^{35}$S ATP and the supplied TTP cycle mix and reaction buffer for 80 PCR cycles with annealing at 55° C. for 45 seconds, and subsequent termination reactions performed for 50 cycles with annealing at 60° C. for 45 seconds.

FIG. 3 HLA-B35 restricted CTL. CTL assay results from donor Z 22 above and donor Z 87 below, both residents of the same village in The Gambia as donors Z 16 and Z 1 (FIG. 2). Cells from donor Z 22 were initially tested (assay 1) on 5 different sets of (1–4) peptides as shown, using as targets a BCL HLA-matched to the donor only for HLA-B35. Cells preincubated with the peptides cp26, cp27 and cp28 were lysed. In assay 2 these peptides and cp29, which are 4 allelic variants (Table 2), were tested individually, again at an effector to target cell ratio of 50:1. Cp26 was recognised, 24.4% specific lysis, and cp28 and 29 were not: cp27 showed 13.7% specific lysis, just below the level we regard as positive, 15%. Cells from donor Z 87 were tested initially on HLA-B35 matched BCL preincubated with seven different peptides, as shown. Significant lysis was found for the cp28, cp29 mixture (54%) and for ls8 (15%); the weak response to cp30 and cp31 was not repeatable. A further assay, using a different BCL again matched only for HLA-B35, confirmed the ls8 result and showed that cp29 but not cp28 was the CSP peptide recognised. CTL from Z 87 also lysed autologous BCL targets preincubated with cp29 and ls8 (not shown). CTL lysis of cp29-pulsed BCL was blocked by the anti-CD8 monoclonal antibody, M236. Using a further sample from donor Z 87, fresh (unrestimulated) PBL were used in a CTL assay on cp29-pulsed targets but no lysis was observed. In all, eight donors with HLA-B35 were tested, all from the village of Brefet, and only these two responded to any of the peptides tested. PBL from two Oxford residents with HLA-B35 were restimulated with all 12 peptides and grew no CTL. All three HLA-B35 epitopes identified here are octamers, with several shared residues, even though most eluted self peptides were nonamers (Table 1). The available data suggest that responses to ls8 in HLA-B35 individuals may be less frequent than ls6 responses in HLA-B53 individuals but larger numbers are required to substantiate this.

To estimate the relative frequencies of the four allelic variants cp26-cp29 in *P. falciparum* in The Gambia. DNA was analyzed from samples collected from 156 children with acute malaria[5]. A segment of the CSP gene containing the DNA encoding this epitope was amplified by PCR and the allelic variants detected by specific oligonucleotide probes. More than one parasite variant (mean 2.0) can frequently be detected in these children with acute malaria[43]. The frequencies of the four variants were:- cp26, 45%; cp27, 78%; cp28, 26%; cp29, 11%.

The single amino acid chances between some of these peptides is sufficient to abolish CTL recognition, as shown in other systems. The poor or absent recognition of cp27 and cp28 appears to result from the charge change at position 5 of the peptide preventing binding to HLA-B35 (not shown).

Methods

Peptide stimulations and CTL assays were performed essentially as described in, the legend to FIG. 2. PBL were incubated with peptides each at 25 μM, pooled as follows: pool 1: the eight CSP peptides cp24-cp31: pool 2: ls2, ls8, tr24 and tr25. All HLA-B35 individuals were typed by the previously described PCR method to confirm that they had the B*3501 rather than the B*3502 or B*3503 subtypes: these latter subtypes are not amplified by the primers used. To identify alleles of the CSP gene by PCR, primers AAT-GCTAATGCCAACAATGCTG (SEQ ID NO:80) and CGA-CATTAAACACACTGGAAC (SEQ ID NO:81) (cf ref. 46) were used (in 1.5 mM MgCl$_2$) with annealing at 58° C. Amplification products were fixed to nitrocellulose filters and alleles [35,46] detected using the following probes with washing in 6xSSC at the stated temperature: cp26, ACGAATTAGATTATGCAA (SEQ ID NO:82) and ACGAATTAGATTATGAAA, (SEQ ID NO:83) 46° C. and 44° C.; cp27, ACCAATTAGATTATGCAA, (SEQ ID NO:84) 46° C.; cp28, ACCAATTAAATTATGAAA, (SEQ ID NO:85) 42° C.; cp29, TAAATCTAAAGACGA, 38° C.

FIG. 4. Peptide concentration titration for CTL specific for the HIV-2 gag peptide, P1 Restimulated CTL were tested on B53 matched target cells at an effector to target ration of 10:1.

Methods

Peripheral blood lymphocytes from HLA-B53 postive, HIV-2 infected adult Gambians were seperated into two populations of 1/8th and 7/8ths and the former fraction was stimulated for 24 hours with phytohaemagglutinin (PHA, Wellcome U.K.) to activate HIV expression and then washed twice before being added back to the unstimulated 7/8th of the cells. This mixed population was cultured for seven days after which lympocult T at 10 U/ml (Biotest U.K.) was added every three days. Target cells were either pulsed with peptide as described above (FIG. 2) or infected with recombinant vaccinia virus at a multiplicity of infection of 3:1. washed twice and resuspended in RPMI 1640 plus 20% foetal calf serum overnight, and assays performed as described (ref 47 and FIG. 2).

We claim:

1. A peptide having the amino acid sequence selected from the group consisting of SEQ ID NO: 1, SEQ ID NO: 2, SEQ ID NO: 5 and SEQ ID NO: 6.

2. A peptide having the amino acid sequence selected from the group consisting of SEQ ID NO: 3, SEQ ID NO: 4 and SEQ ID NO: 7.

* * * * *

SEQUENCE LISTING (1) GENERAL INFORMATION:

(iii) NUMBER OF SEQUENCES: 86

(2) INFORMATION FOR SEQ ID NO: 1:

(i) SEQUENCE CHARACTERISTICS:
      (A) LENGTH: 9 amino acid residues
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Plasmodium falciparum (xi) SEQUENCE DESCRIPTION: SEQ ID NO: 1:

Lys Pro Ile Val Gln Tyr Asp Asn Phe
1              5

(2) INFORMATION FOR SEQ ID NO: 2:

(i) SEQUENCE CHARACTERISTICS:
      (A) LENGTH: 8 amino acid residues
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Plasmodium falciparum (xi) SEQUENCE DESCRIPTION: SEQ ID NO: 2:

Lys Pro Asn Asp Lys Ser Leu Tyr
1              5

(2) INFORMATION FOR SEQ ID NO: 3:

```
    (i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Plasmodium falciparum (xi) SEQUENCE DESCRIPTION: SEQ ID NO: 3:

Lys Pro Lys Asp Glu Leu Asp Tyr
1               5

(2) INFORMATION FOR SEQ ID NO: 4:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Plasmodium falciparum (xi) SEQUENCE DESCRIPTION: SEQ ID NO: 4:

Lys Ser Lys Asp Glu Leu Asp Tyr
1               5

(2) INFORMATION FOR SEQ ID NO: 5:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Plasmodium falciparum (xi) SEQUENCE DESCRIPTION: SEQ ID NO: 5:

Ile Pro Ser Leu Ala Leu Met Leu Ile
1               5

(2) INFORMATION FOR SEQ ID NO: 6:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Plasmodium falciparum (xi) SEQUENCE DESCRIPTION: SEQ ID NO: 6:

Met Pro Leu Glu Thr Gln Leu Ala Ile
1               5

(2) INFORMATION FOR SEQ ID NO: 7:

(i) SEQUENCE CHARACTERISTICS:
        (A) LENGTH: 9 amino acid residues
        (B) TYPE: amino acid
```

```
            (C) STRANDEDNESS: single
            (D) TOPOLOGY: linear (ii) MOLECULE TYPE: peptide (vi) ORIGINAL SOURCE:
            (A) ORGANISM: Plasmodium falciparum (xi) SEQUENCE DESCRIPTION: SEQ ID NO: 7:

Met Pro Asn Asp Pro Asn Arg Asn Val
1               5

(2) INFORMATION FOR SEQ ID NO: 8:

(i) SEQUENCE CHARACTERISTICS:
            (A) LENGTH: 9 amino acid residues
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Human immunodeficiency virus type 2

(xi) SEQUENCE DESCRIPTION: SEQ ID NO: 8:

Thr Pro Tyr Asp Ile Asn Gln Met Leu
1               5

(2) INFORMATION FOR SEQ ID NO: 9:

(i) SEQUENCE CHARACTERISTICS:
            (A) LENGTH: 21 amino acid residues
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 9:

Ala Leu Ser Glu Gly Cys Thr Pro Tyr Asp Ile Asn Gln Met Leu
1               5                   10                  15

Asn Asn Cys Val Gly Asp
                20

(2) INFORMATION FOR SEQ ID NO: 10:

(i) SEQUENCE CHARACTERISTICS:
            (A) LENGTH: 20 amino acid residues
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 10:

His Leu Pro Leu Ser Pro Arg Thr Leu Asn Ala Trp Val Lys Leu
1               5                   10                  15

Ile Glu Glu Lys Lys
                20

(2) INFORMATION FOR SEQ ID NO: 11:

(i) SEQUENCE CHARACTERISTICS:
            (A) LENGTH: 9 amino acid residues
            (B) TYPE: amino acid
            (C) STRANDEDNESS: single
            (D) TOPOLOGY: linear (ii) MOLECULE TYPE: peptide
```

(xi) SEQUENCE DESCRIPTION: SEQ ID NO: 11:

Tyr Pro Ala Glu Ile Thr Leu Tyr Trp
1               5

(2) INFORMATION FOR SEQ ID NO: 12:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Asn Pro Asn Ala Asn Pro Asn Ala
1               5

(2) INFORMATION FOR SEQ ID NO: 13:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Asn Pro Asn Ala Asn Pro Asn Ala Asn
1               5

(2) INFORMATION FOR SEQ ID NO: 14:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Lys Pro Lys His Lys Lys Leu Lys Gln
1               5

(2) INFORMATION FOR SEQ ID NO: 15:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Asn Pro Gly Asp Gly Asn Pro Asp Pro Gly
1               5                   10

(2) INFORMATION FOR SEQ ID NO: 16:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Asn Pro Asp Pro Asn Ala Asn Pro Asn
1               5

(2) INFORMATION FOR SEQ ID NO: 17:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Asp Pro Asn Arg Asn Val Asp Gly Asn
1               5

(2) INFORMATION FOR SEQ ID NO: 18:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Ser Pro Cys Ser Val Thr Cys Gly Asn
1               5

(2) INFORMATION FOR SEQ ID NO: 19:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Lys Pro Gly Ser Ala Asn Lys Pro Lys
1               5

(2) INFORMATION FOR SEQ ID NO: 20:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Lys Pro Lys Asp Glu Leu Asp Tyr Glu
1               5

(2) INFORMATION FOR SEQ ID NO: 21:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Glu Pro Ser Asp Lys His Ile Glu Gln
1               5

(2) INFORMATION FOR SEQ ID NO: 22:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Glu Pro Ser Asp Gln His Ile Glu Lys
1               5

(2) INFORMATION FOR SEQ ID NO: 23:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Glu Pro Ser Asp Lys His Ile Lys Glu
1               5

(2) INFORMATION FOR SEQ ID NO: 24:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Glu Pro Ser Asp Lys His Ile Glu Lys
1               5

(2) INFORMATION FOR SEQ ID NO: 25:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Lys Pro Gly Ser Ala Asp Lys Pro Lys
1               5

(2) INFORMATION FOR SEQ ID NO: 26:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Lys Pro Lys Asp Gln Leu Asp Tyr Ala
1               5

(2) INFORMATION FOR SEQ ID NO: 27:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Lys Pro Lys Asp Glu Leu Asp Tyr Ala
1               5

(2) INFORMATION FOR SEQ ID NO: 28:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Lys Pro Lys Asp Gln Leu Asp Tyr Glu
1               5

(2) INFORMATION FOR SEQ ID NO: 29:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Lys Pro Lys Asp Gln Leu Asp Tyr
1               5

(2) INFORMATION FOR SEQ ID NO: 30:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Glu Pro Ser Asp Gln His Ile Glu
1               5

(2) INFORMATION FOR SEQ ID NO: 31:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Asn Pro Asp Pro Asn Ala Asn Pro Asn Val
1               5                  10

(2) INFORMATION FOR SEQ ID NO: 32:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Asn Pro Asn Val Asp Pro Asn Ala Asn
1               5

(2) INFORMATION FOR SEQ ID NO: 33:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Asp Pro Asn Ala Asn Pro Asn Val Asp
1               5

(2) INFORMATION FOR SEQ ID NO: 34:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Met Pro Asn Tyr Pro Asn Arg Asn Val
1               5

(2) INFORMATION FOR SEQ ID NO: 35:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Met Pro Asn Asn Pro Asn Arg Asn Val
1               5

(2) INFORMATION FOR SEQ ID NO: 36:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Lys Pro Ala Gly Lys Gly Ser Pro Ser
1               5

(2) INFORMATION FOR SEQ ID NO: 37:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Ser Pro Ser Thr Leu Gln Thr Pro Gly
1               5

(2) INFORMATION FOR SEQ ID NO: 38:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Thr Pro Gly Ser Ser Ser Gly Ala Ser
1               5

(2) INFORMATION FOR SEQ ID NO: 39:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Gly Pro Asn Gln Gly Gly Leu Ser Gln
1               5

(2) INFORMATION FOR SEQ ID NO: 40:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Ile Pro Ala Ile Glu Leu Pro Ser Glu
1               5

(2) INFORMATION FOR SEQ ID NO: 41:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide

```
         (xi) SEQUENCE DESCRIPTION: SEQ ID NO: 41:

Leu Pro Ser Glu Asn Glu Arg Gly Tyr
1               5

(2) INFORMATION FOR SEQ ID NO: 42:

(i) SEQUENCE CHARACTERISTICS:
         (A) LENGTH: 9 amino acid residues
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 42:

Ile Pro His Gln Ser Ser Leu Pro Gln
1               5

(2) INFORMATION FOR SEQ ID NO: 43:

(i) SEQUENCE CHARACTERISTICS:
         (A) LENGTH: 9 amino acid residues
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 43:

Leu Pro Gln Asp Asn Arg Gly Asn Ser
1               5

(2) INFORMATION FOR SEQ ID NO: 44:

(i) SEQUENCE CHARACTERISTICS:
         (A) LENGTH: 9 amino acid residues
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 44:

Lys Pro Glu Gln Lys Glu Asp Lys Ser
1               5

(2) INFORMATION FOR SEQ ID NO: 45:

(i) SEQUENCE CHARACTERISTICS:
         (A) LENGTH: 9 amino acid residues
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 45:

Lys Pro Asn Asp Lys Ser Leu Tyr Asp
1               5

(2) INFORMATION FOR SEQ ID NO: 46:

(i) SEQUENCE CHARACTERISTICS:
         (A) LENGTH: 8 amino acid residues
         (B) TYPE: amino acid
         (C) STRANDEDNESS: single
         (D) TOPOLOGY: linear (ii) MOLECULE TYPE: peptide
```

(xi) SEQUENCE DESCRIPTION: SEQ ID NO: 46:

Lys Pro Ile Val Gln Tyr Asp Asn
1               5

(2) INFORMATION FOR SEQ ID NO: 47:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Ser Pro Cys Ser Val Thr Cys Gly Lys
1               5

(2) INFORMATION FOR SEQ ID NO: 48:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Lys Pro Asn Ile Pro Glu Asp Ser Glu Lys
1               5                   10

(2) INFORMATION FOR SEQ ID NO: 49:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Ile Pro Tyr Ser Pro Leu Pro Pro Lys
1               5

(2) INFORMATION FOR SEQ ID NO: 50:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Glu Pro Ser Pro Asn Pro Glu Glu Gly Lys
1               5                   10

(2) INFORMATION FOR SEQ ID NO: 51:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

His Pro Glu Arg Glu Glu His Glu Lys
1               5

(2) INFORMATION FOR SEQ ID NO: 52:

(i) SEQUENCE CHARACTERISTICS:
           (A) LENGTH: 10 amino acid residues
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 52:

Asn Pro Glu Asn Pro Pro Asn Pro Asp Ile
1               5                   10

(2) INFORMATION FOR SEQ ID NO: 53:

(i) SEQUENCE CHARACTERISTICS:
           (A) LENGTH: 9 amino acid residues
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 53:

Val Pro Lys Asn Pro Glu Asp Asp Arg
1               5

(2) INFORMATION FOR SEQ ID NO: 54:

(i) SEQUENCE CHARACTERISTICS:
           (A) LENGTH: 9 amino acid residues
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 54:

Pro Pro Lys Val Leu Asp Asn Glu Arg
1               5

(2) INFORMATION FOR SEQ ID NO: 55:

(i) SEQUENCE CHARACTERISTICS:
           (A) LENGTH: 10 amino acid residues
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 55:

Val Pro Asn Ser Glu Asp Arg Glu Thr Arg
1               5                   10

(2) INFORMATION FOR SEQ ID NO: 56:

(i) SEQUENCE CHARACTERISTICS:
           (A) LENGTH: 10 amino acid residues
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 56:

Arg Pro His Gly Arg Asn Asn Glu Asn Arg
1               5                   10

(2) INFORMATION FOR SEQ ID NO: 57:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Glu Pro Glu Asp Asp Gln Pro Arg Pro Arg
1               5                   10

(2) INFORMATION FOR SEQ ID NO: 58:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Leu Pro Pro Lys Val Leu Asp Asn Glu Arg
1               5                   10

(2) INFORMATION FOR SEQ ID NO: 59:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

Ile Pro Asp Ser Ile Gln Asp Ser Leu
1               5

(2) INFORMATION FOR SEQ ID NO: 60:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

Ile Pro Glu Asp Ser Glu Lys Glu Val
1               5

(2) INFORMATION FOR SEQ ID NO: 61:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

Glu Pro Ala Pro Phe Asp Glu Thr Leu
1               5

(2) INFORMATION FOR SEQ ID NO: 62:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Val Pro Asp Glu Pro Glu Asp Asp Gln
1               5

(2) INFORMATION FOR SEQ ID NO: 63:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

Ile Pro Lys Lys Pro Glu Asn Lys His
1               5

(2) INFORMATION FOR SEQ ID NO: 64:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

Thr Pro Lys His Pro Glu Arg Glu Glu
1               5

(2) INFORMATION FOR SEQ ID NO: 65:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

His Pro Ser Asp Gly Lys Cys Asn Leu
1               5

(2) INFORMATION FOR SEQ ID NO: 66:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

Gly Pro Phe Met Lys Ala Val Cys Val
1               5

(2) INFORMATION FOR SEQ ID NO: 67:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

Pro Pro Lys Trp Glu Pro Leu Asp Val
1               5

(2) INFORMATION FOR SEQ ID NO: 68:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

Lys Pro Lys Asp Gln Leu Asp Tyr
1               5

(2) INFORMATION FOR SEQ ID NO: 69:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

Lys Pro Lys Asp Gln Leu Asn Tyr
1               5

(2) INFORMATION FOR SEQ ID NO: 70:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 70:

Glu Pro Ser Asp Lys His Ile Glu Gln Tyr
1               5                   10

(2) INFORMATION FOR SEQ ID NO: 71:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Glu Pro Ser Asp Gln His Ile Glu Lys Tyr
1               5                   10

(2) INFORMATION FOR SEQ ID NO: 72:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

His Pro Ser Asp Gly Lys Cys Asn Leu Tyr
1               5                   10

(2) INFORMATION FOR SEQ ID NO: 73:

(i) SEQUENCE CHARACTERISTICS:
        (A) LENGTH: 8 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Val Pro Gly Ala Ala Thr Pro Tyr
1               5

(2) INFORMATION FOR SEQ ID NO: 74:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Tyr Pro Ala Glu Ile Thr Leu Thr Trp
1               5

(2) INFORMATION FOR SEQ ID NO: 75:

(i) SEQUENCE CHARACTERISTICS:
        (A) LENGTH: 15 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Glu Asn Asp Ile Glu Lys Lys Ile Cys Lys Met Glu Lys Cys Ser
1               5                   10                  15

(2) INFORMATION FOR SEQ ID NO: 76:

(i) SEQUENCE CHARACTERISTICS:
        (A) LENGTH: 15 amino acid residues
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

Glu Leu Asp Tyr Ala Asn Asp Ile Glu Lys Lys Ile Cys Lys Met
1               5                   10                  15

(2) INFORMATION FOR SEQ ID NO: 77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 77:

GTGCTGAATA TGACGATTCA                                           20

(2) INFORMATION FOR SEQ ID NO: 78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 78:

CCTTTTCCTT ATTAACCTGC                                           20

(2) INFORMATION FOR SEQ ID NO: 79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 79:

TTCCTTCATC TAAATCATCT                                           20

(2) INFORMATION FOR SEQ ID NO: 80:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 80:

AATGCTAATG CCAACAATGC TG                                        22

(2) INFORMATION FOR SEQ ID NO: 81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 81:

CGACATTAAA CACACTGGAA C                                         21

(2) INFORMATION FOR SEQ ID NO: 82:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 82:

ACGAATTAGA TTATGCAA                                                  18

(2) INFORMATION FOR SEQ ID NO: 83:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 83:

ACGAATTAGA TTATGAAA                                                  18

(2) INFORMATION FOR SEQ ID NO: 84:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 84:

ACCAATTAGA TTATGCAA                                                  18

(2) INFORMATION FOR SEQ ID NO: 85:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 85:

ACCAATTAAA TTATGAAA                                                  18

(2) INFORMATION FOR SEQ ID NO: 86:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 86:

TAAATCTAAA GACGA                                                    15